United States Patent
Kim et al.

(10) Patent No.: US 10,058,391 B2
(45) Date of Patent: Aug. 28, 2018

(54) MOTION CONTROL SYSTEM FOR MODULE TYPE CAPSULE ROBOT IN BODY

(71) Applicant: KOREA INSTITUTE OF SCIENCE AND TECHNOLOGY, Seoul (KR)

(72) Inventors: Laehyun Kim, Seoul (KR); Sung Chul Kang, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 811 days.

(21) Appl. No.: 14/496,830

(22) Filed: Sep. 25, 2014

(65) Prior Publication Data
US 2015/0105797 A1    Apr. 16, 2015

(30) Foreign Application Priority Data
Oct. 10, 2013   (KR) .......................... 10-2013-0120290

(51) Int. Cl.
*A61B 1/04*      (2006.01)
*A61B 19/00*    (2006.01)
(Continued)

(52) U.S. Cl.
CPC ...... *A61B 19/2203* (2013.01); *A61B 1/00156* (2013.01); *A61B 1/00158* (2013.01);
(Continued)

(58) Field of Classification Search
USPC .... 600/114, 115, 153–159; 604/95.01–95.05
See application file for complete search history.

(56) References Cited

U.S. PATENT DOCUMENTS 4,176,662 A * 12/1979 Frazer ................ A61B 1/00156
                                                                138/103
5,398,670 A *  3/1995 Ortiz .................. A61B 1/00156
                                                                385/119
(Continued)

FOREIGN PATENT DOCUMENTS

JP           2002-556 A      1/2002
KR      10-0702155 B1      4/2007
(Continued)

OTHER PUBLICATIONS

Meron, Gavriel D. "The development of the swallowable video capsule (M2A)." Gastrointestinal endoscopy 52.6 (2000): 817-819.
(Continued)

*Primary Examiner* — Matthew J Kasztejna
(74) *Attorney, Agent, or Firm* — NSIP Law

(57) ABSTRACT

A motion control system includes a first capsule robot, which includes a first housing, a first shaft configured to be movable bi-directionally, the first shaft having a first permanent magnet at an outer end, a first leg unit configured to protrude outwards from the first housing, and a first control unit; and a second capsule robot, which includes a second housing, a second shaft configured to be movable bi-directionally, the second shaft having a second permanent magnet at an outer end, a second leg unit, and a second control unit, wherein the first capsule robot is fixed with respect to an the internal organ wall by protruding the first leg unit to the internal organ, and wherein the second capsule robot is connected to the first capsule robot as the first permanent magnet comes into contact with the second permanent magnet by an attractive force.

14 Claims, 4 Drawing Sheets

(51) Int. Cl.
  *A61B 1/00*  (2006.01)
  *A61B 34/30* (2016.01)
  *A61B 34/00* (2016.01)

(52) U.S. Cl.
  CPC .............. *A61B 1/041* (2013.01); *A61B 34/30* (2016.02); *A61B 2034/303* (2016.02); *A61B 2034/733* (2016.02); *Y10S 901/01* (2013.01)

(56) References Cited

U.S. PATENT DOCUMENTS

| | | | | |
|---|---|---|---|---|
| 5,662,587 | A * | 9/1997 | Grundfest | A61B 1/00082 600/114 |
| 6,162,171 | A * | 12/2000 | Ng | A61B 1/00156 600/101 |
| 6,240,312 | B1 * | 5/2001 | Alfano | A61B 1/00016 128/903 |
| 6,648,814 | B2 * | 11/2003 | Kim | A61B 1/00156 356/241.6 |
| 6,719,684 | B2 * | 4/2004 | Kim | A61B 1/00016 600/101 |
| 6,764,441 | B2 * | 7/2004 | Chiel | A61B 1/00156 600/115 |
| 6,911,004 | B2 * | 6/2005 | Kim | A61B 1/00156 600/101 |
| 6,951,536 | B2 * | 10/2005 | Yokoi | A61B 1/00016 348/E5.026 |
| 7,678,043 | B2 * | 3/2010 | Gilad | A61B 1/00156 600/109 |
| 7,727,145 | B2 * | 6/2010 | Yokoi | A61B 1/00016 600/109 |
| 7,998,060 | B2 | 8/2011 | Ferren et al. | |
| 8,160,680 | B2 | 4/2012 | Boyden et al. | |
| 2004/0133076 | A1 * | 7/2004 | Kobayashi | A61B 1/00016 600/175 |

FOREIGN PATENT DOCUMENTS

| | | |
|---|---|---|
| KR | 10-2008-0009988 A | 1/2008 |
| WO | WO 2006/121239 A1 | 11/2006 |

OTHER PUBLICATIONS

Park, Hyunjun, et al. "Paddling based microrobot for capsule endoscopes." Robotics and Automation, 2007 IEEE International Conference on. IEEE, 2007. 3377-3382.

Quirini, Marco, et al. "Design and fabrication of a motor legged capsule for the active exploration of the gastrointestinal tract." Mechatronics, IEEE/ASME Transactions on 13.2 (2008): 169-179.

Park, Sunkil, et al. "A novel microactuator for microbiopsy in capsular endoscopes." Journal of Micromechanics and Microengineering 18.2 (2008): 025032. (10 pages).

Nagy, Z., et al. "Assembling reconfigurable endoluminal surgical systems: opportunities and challenges." International Journal of Biomechatronics and Biomedical Robotics 1.1 (2009): 3-16.

Rammohan, Ashwin, et al. "Capsule endoscopy: New technology, old complication." Journal of surgical technique and case report 3.2 (2011). 91-93.

Kim, Laehyun, et al. "Prototype modular capsule robots for capsule endoscopies." Control, Automation and Systems (ICCAS), 2013 13th International Conference on. IEEE, 2013. (5 pages).

* cited by examiner

MOTION CONTROL SYSTEM FOR MODULE TYPE CAPSULE ROBOT IN BODY

CROSS-REFERENCE TO RELATED APPLICATION

This application claims priority to Korean Patent Application No. 10-2013-0120290, filed on Oct. 10, 2013, and all the benefits accruing therefrom under 35 U.S.C. § 119, the contents of which in its entirety are herein incorporated by reference.

BACKGROUND

1. Field

The present disclosure relates to a system for controlling an operation of a module type capsule robot in a body, and more particularly, to a system for controlling an operation of a module type capsule robot in a body, which alternately fixes capsule robots, interconnected by permanent magnets, to an internal organ wall to be moved in one direction.

2. Description of the Related Art

Endoscopy is a representative medical procedure for diagnosing and treating a digestive system. Recently, a doctor directly observes the digestive system by using a long and bent tool having a camera, which allows more accurate determination in comparison to an existing image technology (using angiographic, ultrasonic wave, X-ray or the like). However, such a traditional endoscopy may give serious inconvenience to a patient and is not able to inspect the small intestine due to its physical limit.

In the current clinical trials, the wireless capsule endoscopy and the deep small bowl endoscopy are used for inspect the small intestine. First, in the wireless capsule endoscopy, after a patient swallow a small capsule-type endoscopic tool, the endoscopic tool in a human body due to intestinal mobility, and a camera included therein takes pictures periodically or in proportion to a moving speed during the movement and sends the pictures to an external storage device wirelessly. After that, a doctor analyzes the stored pictures and determines abnormality. However, this capsule endoscope is not capable of adjusting a location, speed, direction or the like of the capsule, which often makes it difficult to obtain so sufficient information to determine abnormality, and additional treatments such as biopsy and polypectomy cannot be performed.

As another method, the deep small bowl endoscopy capable of inspecting a small intestine is used at clinical trials. However, the deep small bowl endoscopy is somewhat invasive and causes inconvenience of a patient and hard work of an operator due to a long inspection time of 1 to 2 hours, and it is frequently difficult to insert the tool or remove the polypus since the endoscope is long and forms a loop.

To overcome such drawbacks, endoscopies in which a robot technology is employed to a capsule robot endoscope are being studied. However, in order to apply the endoscopies to actual medical spots, some obstacles should be overcome.

First, due to the limit of a capsule size, it is difficult to accommodate various functions such as a camera module, a movement module, a power module, a wireless communication module, a biopsy module or the like in a small capsule. Accordingly, a complicated design is demanded, and there is a limit in applying this technique to a surgical treatment which needs multi-degree of mobility freedom.

Second, it is difficult to implement an effective movement mechanism in a digestive internal organ (a small intestine and a large intestine) which is smooth and has irregular environments. Even though a movement mechanism has been implemented and manifested in various studies which have been performed in the art, there are many limits in application to an actual medical spot since the capsule has an increased size and does not has a desired speed or function.

Third, since various functions such as a movement mechanism are included in a single capsule robot, a great power is demanded. For this reason, a large battery should be increased or a separate battery module should be carried.

The assembling reconfigurable endoluminal surgical (ARES) recently introduced in the art is an assembly-type robot platform. Here, ten or more robot modules are swallowed by a patient and then assembled in the stomach into a specific structure to perform inspection or treatment. Until now, the assembling reconfigurable endoluminal surgical is a proto type which just shows its concept, and an operating mechanism for actual assembling or treating has not been proposed. In addition, since a patient should swallow ten or more robot modules, the patient inevitably feels inconvenience and it is not easy to remove the robot modules. In addition, there is no detailed explanation in relation to interactive operations of the capsule robots in a narrow and smooth environment in a small intestine or a large intestine, other than the stomach.

RELATED LITERATURES

Non-Patent Literature

G. D. Meron, "The development of the swallowable video capsule (M2A)", Gastrointestinal Endoscopy, Vol. 52, No. 6, pp. 817-819, 2000.

S. Park, et al., "A novel micro actuator for micro biopsy in capsular endoscopes", Journal of Micromechanics and Microengineering, Vol. 18, No. 2, pp 250-260, 2008.

Z. Nagy, et al., "Assembling reconfigurable endoluminal surgical systems: opportunities and challenges", Int. J. Biomechatronics and Biomedical Robotics, Vol. 1, No. 1, 2009

SUMMARY

The present disclosure is directed to providing a structure which allows functionally modularized capsule robots to be selected as necessary and swallowed and a detailed mechanism for allowing the capsule robots to be united, moved or separated in the digestive internal organ.

In one aspect, there is provided a motion control system for a module type capsule robot in a body, comprising a first capsule robot, which includes a first housing configuring an appearance, a first shaft configured to be movable bi-directionally along a first extension hole formed in one surface of the first housing, the first shaft having a first permanent magnet at an outer end thereof, a first leg unit configured to protrude outwards from the first housing and be inserted again into the first housing, and a first control unit for controlling operations of the first shaft and the first leg unit; and a second capsule robot, which includes a second housing configuring an appearance, a second shaft configured to be movable bi-directionally along a second extension hole formed in one surface of the second housing, the second shaft having a second permanent magnet at an outer end thereof, a second leg unit configured to protrude outwards from the second housing and be inserted again into the second housing, and a second control unit for controlling operations of the second shaft and the second leg unit, wherein the first capsule robot is fixed with respect to an the internal organ wall by protruding the first leg unit to the internal organ wall at a predetermined location in an internal organ, and wherein the second capsule robot is connected to the first capsule robot as the first permanent magnet comes into contact with the second permanent magnet by an attractive force.

In addition, in the motion control system for a capsule robot in a body, the first shaft may further include a hinge between the first permanent magnet and the outer end of the first shaft so that the first permanent magnet becomes rotatable.

In addition, in the motion control system for a capsule robot in a body, the outer end of the first leg unit and the outer end of the second leg unit may be made of soft plastic or rubber.

In addition, in the motion control system for a capsule robot in a body, the second capsule robot may be fixed with respect to the internal organ wall by protruding the second leg unit to the internal organ wall in a state of being connected to the first capsule robot, the first capsule robot may move by a predetermined length by inserting the protruded first leg unit into the first housing and moving the first shaft out of the first capsule robot, and after that, the first capsule robot may be fixed with respect to the internal organ wall at the location moved by a predetermined length by protruding the inserted first leg unit to the internal organ wall.

In addition, in the motion control system for a capsule robot in a body, the second capsule robot may be fixed with respect to the internal organ wall by protruding the second leg unit to the internal organ wall in a state of being connected to the first capsule robot, the first capsule robot may insert the protruded first leg unit into the first housing, the second capsule robot may move the first capsule robot by a predetermined length in a direction opposite to the second capsule robot by moving the second shaft out of the second capsule robot, and after that, the first capsule robot may be fixed with respect to the internal organ wall at the location moved by a predetermined length by protruding the inserted first leg unit to the internal organ wall.

In addition, in the motion control system for a capsule robot in a body, the second capsule robot may move toward the first capsule robot by a predetermined length by inserting the protruded second leg unit into the second housing and moving the second shaft into the second capsule robot.

In addition, in the motion control system for a capsule robot in a body, the second capsule robot may insert the protruded second leg unit into the second housing, and the first capsule robot may move the second capsule robot toward the first capsule robot by a predetermined length by moving the first shaft into the first capsule robot.

In addition, in the motion control system for a capsule robot in a body, the second capsule robot may be fixed with the internal organ wall by protruding the second leg unit to internal organ wall in a state of being connected to the first capsule robot, the first capsule robot may move toward the second capsule robot by a predetermined length by inserting the protruded first leg unit into the first housing and moving the first shaft into the first capsule robot, and after that, the first capsule robot may be fixed with respect to the internal organ wall at the location moved by a predetermined length by protruding the inserted first leg unit to internal organ wall.

In addition, in the motion control system for a capsule robot in a body, the second capsule robot may be fixed with the internal organ wall by protruding the second leg unit to internal organ wall in a state of being connected to the first capsule robot, the first capsule robot may insert the protruded first leg unit into the first housing, the second capsule robot may move the first capsule robot toward the second capsule robot by a predetermined length by moving the second shaft into the second capsule robot, and after that, the first capsule robot may be fixed with respect to the internal organ wall at the location moved by a predetermined length by protruding the inserted first leg unit to internal organ wall.

In addition, in the motion control system for a capsule robot in a body, the second capsule robot may move by a predetermined length in a direction opposite to the first capsule robot by inserting the protruded second leg unit into the second housing and moving the second shaft out of the second capsule robot, and after that, the second capsule robot may be fixed with respect to the internal organ wall at the location moved by a predetermined length by protruding the inserted second leg unit to the internal organ wall.

In addition, in the motion control system for a capsule robot in a body, the second capsule robot may move by a predetermined length in a direction opposite to the first capsule robot by inserting the protruded second leg unit into the second housing and moving the first shaft out of the first capsule robot, and after that, the second capsule robot may be fixed with respect to the internal organ wall at the location moved by a predetermined length by protruding the inserted second leg unit to the internal organ wall.

In addition, in the motion control system for a capsule robot in a body, the first capsule robot may be fixed with respect to the internal organ wall by protruding the first leg unit to the internal organ wall, the second capsule robot may be fixed with respect to the internal organ wall by protruding the second leg unit to the internal organ wall, the first capsule robot may move the first shaft into the first capsule robot, and the second capsule robot may move the second shaft into the second capsule robot so that first capsule robot and the second capsule robot are separated from each other.

In addition, in the motion control system for a capsule robot in a body, the first capsule robot may insert the first leg unit into the first housing or the second capsule robot may insert the second leg unit into the second housing, whereby the first capsule robot or the second capsule robot is separated from the internal organ wall.

In addition, in the motion control system for a capsule robot in a body, the first capsule robot may further include a first camera at one surface thereof, and the second capsule robot may further include a second camera at one surface thereof.

In addition, in the motion control system for a capsule robot in a body, the first capsule robot and the second capsule robot may further include a first communication module and a second communication module, respectively, an external control device not inserted into the internal organ may be further provided, the external control device may transmit an operation command or power to the first control unit and the second control unit, and the first control unit and the second control unit may control the first capsule robot and the second capsule robot, respectively, according to the operation command.

In addition, in the motion control system for a capsule robot in a body, the first capsule robot and the second capsule robot may further include a first communication module and a second communication module, respectively, an external control device not inserted into the internal organ may be further provided, the first communication module or the second communication module may transmit image data, obtained from the first camera or the second camera, to the external control device, and the external control device may include a display device for displaying the transmitted data and a database for storing the transmitted data.

In addition, in the motion control system for a capsule robot in a body, the second capsule robot may further include a fourth extension hole formed at a side opposite to the second extension hole; and a fourth shaft configured to be movable bi-directionally along the fourth extension hole, the fourth shaft having a fourth permanent magnet at an outer end thereof, wherein the motion control system may further comprise a third capsule robot, which includes a third housing configuring an appearance, a third shaft configured to be movable directionally along a third extension hole formed at one surface of the third housing, the third shaft having a third permanent magnet at an outer end thereof, a third leg unit configured to protrude outwards from the third housing and be inserted again into the third housing, a third communication module configured to transmit or receive a signal to/from another party, and a third control unit for controlling operations of third shaft, the third leg unit and the third communication module, and the third capsule robot may be connected to the second capsule robot as the fourth permanent magnet comes into contact with the third permanent magnet by an attractive force.

According to an embodiment of the present disclosure, since two or more capsule robots are united in an internal organ, it is possible to put capsule robots, each having one necessary function, individually and allows the capsule robots to be interconnected in the internal organ. Here, the capsule robots may move bi-directionally by means of an inchworm movement mechanism as described above, and a robot assembly having a multi-degree of mobility freedom may be used by connecting three or more capsule robots. Therefore, the capsule robots may freely move in the internal organ, and capsule robots having various functions may be used.

In addition, the limit in a module size may be overcome by dispersing a movement mechanism to two capsule robots, and power consumption is relatively low since a relatively simple mechanism may be used. In detail, by realizing an inchworm mechanism in which two robot modules are united and then move by pushing or pulling each other, the robot modules may move a double distance in comparison to a single capsule, which ensures faster movement.

In addition, even though an existing single capsule robot is generally capable of moving only in a forward direction, the mechanism proposed in the present disclosure allows bi-directional movement, which allows repeated inspection at a desired location.

DETAILED DESCRIPTION

Figure 1:
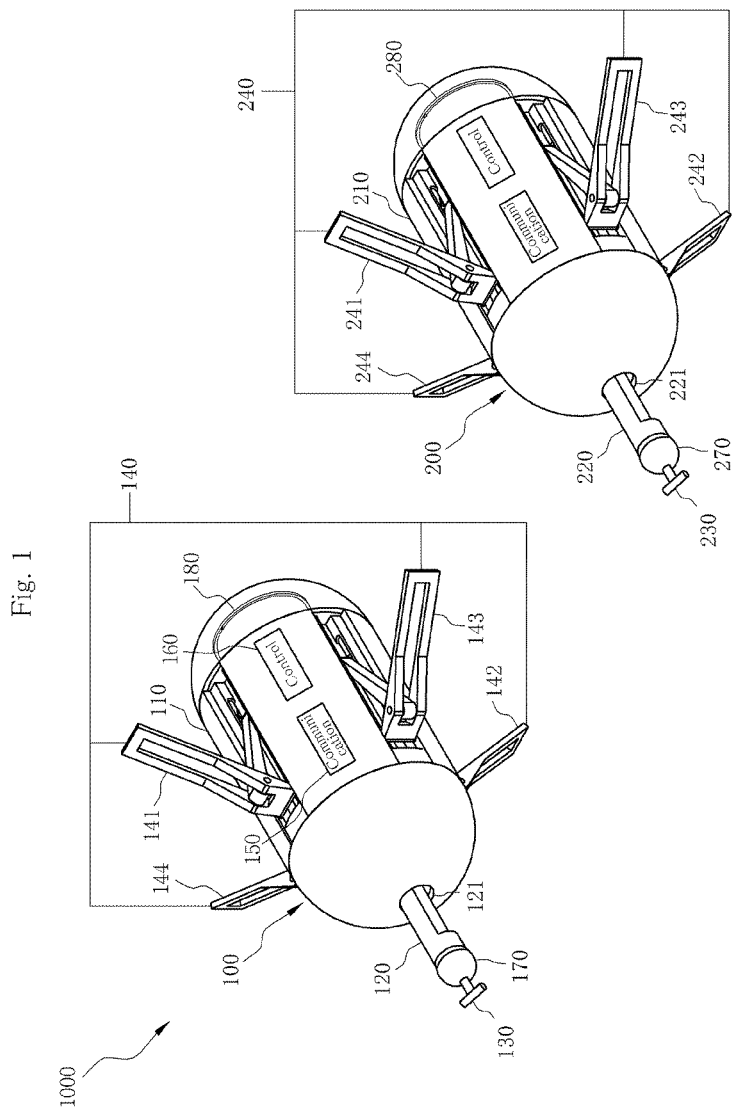
FIG. 1 is a perspective view showing a motion control system for a capsule robot in a body according to an embodiment of the present disclosure.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein. In the drawings, like reference numerals denote like elements. In the description, details of well-known features and techniques may be omitted to avoid unnecessarily obscuring the presented embodiments. In addition, the shape, size and regions, and the like, of the drawing may be exaggerated for clarity.

Embodiments set forth in this specification may be totally hardware, partially software and partially hardware, or totally software. In this specification, the terms "unit", "module", "device", "system" or the like represent computer-related entities such as hardware, a combination of hardware and software, or software. For example, in this specification, the terms "unit", "module", "device", "system" or the like may represent a process in execution, a processor, an object, an executable file, a thread of execution, a program and/or a computer, without being limited thereto. For example, both an application in execution and a computer may be employed as a unit, a module, a device or a system in this specification.

Hereinafter, embodiments of the present disclosure will be described in detail with reference to the drawings.

FIG. 1 is a perspective view showing a motion control system for a capsule robot in a body according to an embodiment of the present disclosure. The motion control system 1000 for a capsule robot in a body according to an embodiment may include two or more capsule robots which are put into a body and operate therein.

The motion control system 1000 for a capsule robot in a body according to an embodiment as shown in FIG. 1 includes a first capsule robot 100 and a second capsule robot 200. The capsule robots are put into a body as a patient swallows them.

The capsule robots put into a body may be combined at a specific location in the body and move in a specific direction. The capsule robots may be combined and perform various operations such as movement in a specific direction according to a signal input from an external control device or a preset command.

Referring to FIG. 1, in the motion control system 1000 for a capsule robot in a body according to an embodiment, the first capsule robot 100 includes a first housing 110 configuring an appearance, a first shaft 120 configured to be movable bi-directionally along a first extension hole 121 formed in one surface of the first housing, a first leg unit 140 configured to protrude out of the first capsule robot from the first housing and be inserted again into the first housing, and a first control unit 160 for controlling operations of the first shaft and the first leg unit, and a first permanent magnet 130 is provided at an outer end of the first shaft 120. In another embodiment, the first capsule robot 100 may further include a first communication module 150 configured to transmit or receive a signal to/from another party, and the first communication module may be controlled by the first control unit.

In the motion control system 1000 for a capsule robot in a body according to an embodiment, similar to the first capsule robot 100, the second capsule robot 200 includes a second housing 210 configuring an appearance, a second shaft 220 configured to be movable bi-directionally along a second extension hole formed in one surface of the second housing, a second leg unit 240 configured to protrude outwards from the second housing and be inserted again into the second housing, and a second control unit 260 for controlling operations of the second shaft and the second leg unit, and the second shaft 120 has a second permanent magnet 230 at an outer end thereof. In another embodiment, the second capsule robot 200 may further include a second communication module 250 configured to transmit or receive a signal to/from another party, and the second communication module may be controlled by the second control unit.

The first housing 110 configures an appearance of the first capsule robot 100. The first housing 110 may be made of any material which does not harm the body of a patient when being put therein. In addition, the first housing 110 may have a size which ensures passage through each body organ of the patient. For example, the first capsule robot 100 may be sized so as to be swallowed by a patient and discharged through the anus of the patient.

The first housing 110 may have spherical, regular hexahedral or other various three-dimensional shapes. In addition, the first housing 110 may have a streamlined shape to ensure smooth movement in a body, more preferably a capsule shape as shown in FIG. 1.

The first extension hole 121 may be formed in one surface of the first housing 110 of the first capsule robot 100. For example, as shown in FIG. 1, the first extension hole 121 may be formed in one surface in a length direction of the first capsule robot 100.

The first shaft 120 is movable bi-directionally along the first extension hole. The bi-directional movement of the first shaft 120 may be controlled by the first control unit 160. In detail, the first control unit 160 may include a motor (not shown), and the first control unit 160 may move the first shaft 120 bi-directionally in a horizontal direction by using the motor. When the first shaft 120 moves into the first capsule robot 100, a protruded length of the first shaft 120 decreases, and when the first shaft 120 moves out of the first capsule robot 100, the protruded length of the first shaft 120 increases as much.

The length of the first shaft 120 protruding out of the first housing 110 may be adjusted as desired. For example, before the first capsule robot performs a specific behavior in a body, the first shaft 120 may be entirely inserted into the first housing 110.

An inner end of the first shaft 120 is located in the first housing 110, and its outer end of the first shaft 120 is located out of the first housing 110. As shown in FIG. 1, the first permanent magnet 130 may be provided at the outer end of the first shaft 120.

In addition, in another embodiment, a hinge 170 may be provided between the first shaft 120 and the first permanent magnet 130. By providing the hinge 170, the first permanent magnet 130 may rotate in a state of being fixed to the first shaft.

If the first capsule robot 100 and the second capsule robot 200 are connected by means of the first permanent magnet 130, the hinge 170 functions as a joint so that the first capsule robot 100 and the second capsule robot 200 may be connected in a bent state (namely, with a predetermined angle between them).

In an embodiment, the first leg unit 140 may include one or more first leg 141, 142, 143 .... The first leg unit 140 may include two or more legs. The first leg unit 140 of FIG. 1 includes four first legs at 90°, but this is just an example.

The first leg of the first leg unit 140 may protrude out of the first housing 110 and then be inserted into the first housing 110 again. The protruded length of the first leg may vary depending on the usage of the capsule robot. For example, if a main purpose of the capsule robot is an operation in a small intestine, the first leg unit protrudes by a length so that the first capsule robot steps on the small intestine and is fixed thereto. In addition, in an embodiment, the outer end of the first leg unit 140 may be made of a material such as soft plastic or rubber which does not harm the internal organ wall. Since the outer end of the first leg unit is coated with a rubber material, even though the first leg unit pushes the internal organ wall of a patient, the internal organ wall may not be seriously stressed.

The first leg unit 140 depicted in FIG. 1 may protrude out or be inserted inwards by folding toward the first housing 110 or unfolding therefrom. However, the configuration depicted in FIG. 1 is just an example, and the first leg unit 140 may protrude out of the first housing 110 or be inserted therein in various ways. For example, similar to the operation of the first shaft 120, the first legs of the first leg unit 140 may protrude or be inserted through the hole formed in the surface of the first housing 110.

The first communication module 150 may transmit or receive a signal to/from another party. In detail, the first communication module 150 may communicate with any control device present out of the body of a patient or another capsule robot. For example, the first communication module 150 may transmit information obtained in the body of a patient to a control device present out of the body of a patient or receive a command from the control device. In other cases, the first communication module 150 may exchange information about a location or state of another capsule robot. For this communication, the first communication module 150 may use any communication method.

The first control unit 160 may control operations of the first shaft, the first leg unit and the first communication module. The first control unit 160 may centrally control operations or information exchange of any or all components (for example, cameras or any operating devices) included in the first capsule robot 100. As described above, the first control unit 160 may include a driving motor and accordingly may directly perform mechanical operations of the first capsule robot 100.

In an embodiment, each component of the second capsule robot 200 may be identical or similar to each component of the first capsule robot. In other words, the first housing 110 and the second housing 210, the first shaft 120 and the second shaft 220, the first permanent magnet 130 and the second permanent magnet 230, the first leg unit 140 and the second leg unit 240, the first communication module 150 and the second communication module 250, and the first control unit 160 and the second control unit 260 may correspond to each other, and as described above, each component of the second capsule robot 200 may operate or function with a structure identical or similar to that of each component of the first capsule robot.

In the motion control system for a capsule robot in a body according to an embodiment of the present disclosure, the capsule robots are interconnected in an internal organ and move in a specific direction. Hereinafter, a mechanism of connecting, separating and moving the capsule robots will be described.

[Uniting and Moving of Capsule Robots]

Figure 2:
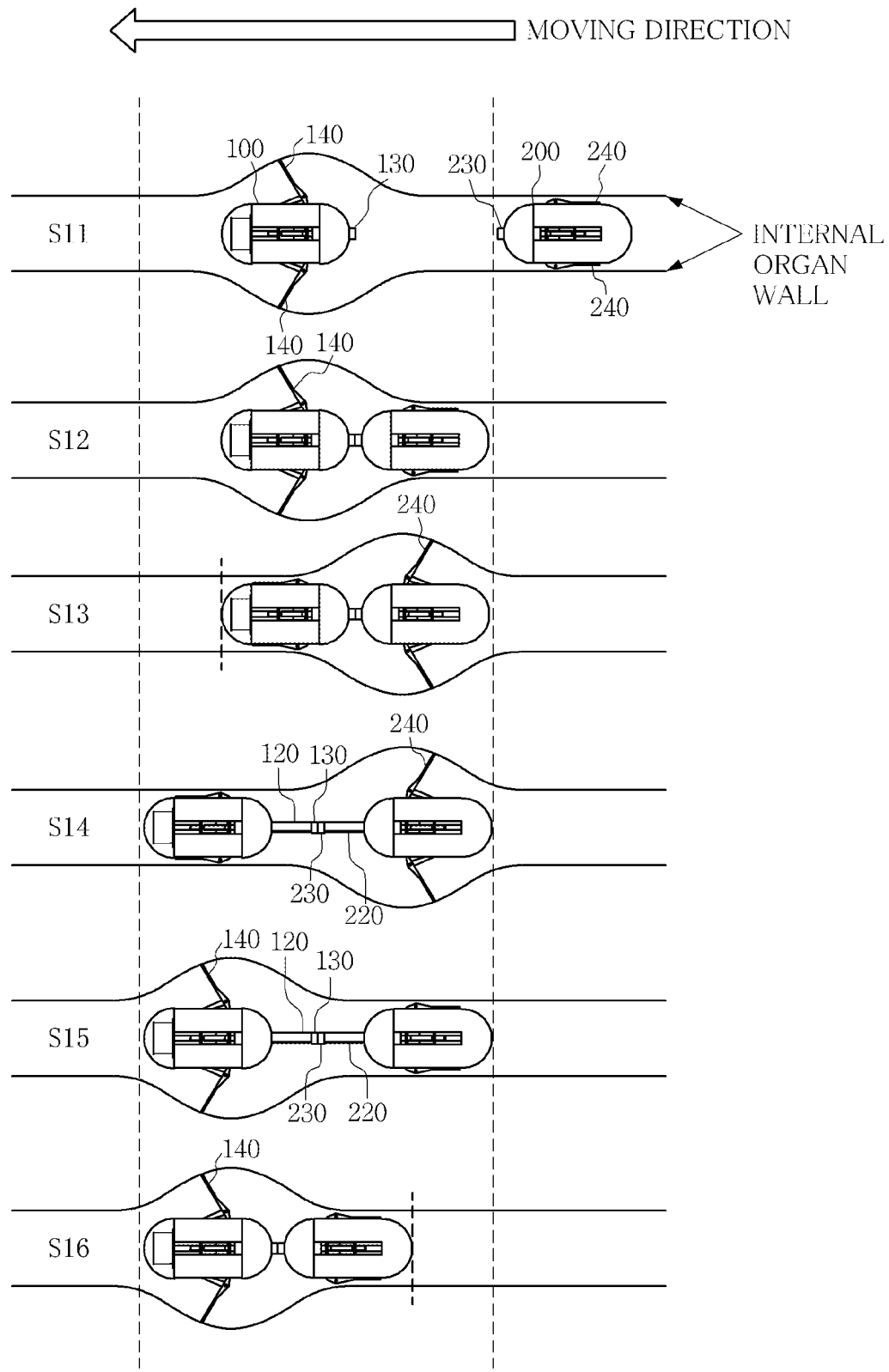
FIG. 2 is a diagram for illustrating a connection and movement mechanism of capsule robots, employed in the motion control system for a capsule robot in a body according to an embodiment of the present disclosure.

FIG. 2 is a diagram for illustrating a connection and movement mechanism of capsule robots, employed in the motion control system for a capsule robot in a body according to an embodiment of the present disclosure. Referring to FIG. 2, each Step S11-S16 of this embodiment shows operation and location of the capsule robots 100, 200 in the time order. In FIG. 2, a dotted line represents a location in the same internal organ. The movement of the capsule robot 100 may be checked with reference to the dotted line.

First, the first capsule robot 100 and the second capsule robot 200 may be put into a body in order. In Step S11, the first capsule robot 100 may be fixed with respect to the internal organ wall at a predetermined location in the internal organ by protruding the first leg unit 140 to the internal organ wall. Since the first capsule robot 100 moving ahead along the internal organ wall stops this specific location, the following second capsule robot 200 may encounter the first capsule robot 100.

In Step S12, in a state where the first capsule robot 100 is fixed at a specific location, the second capsule robot 200 moves near the first capsule robot 100 by means of mobility of the internal organ or the movement of the second capsule robot 200 and is connected to the first capsule robot since the first permanent magnet 130 and the second permanent magnet 230 come into contact with each other by an attractive force. In other words, the protruded portion of the first shaft 120 and the protruded portion of the second shaft 220 come into contact with each other by means of the first permanent magnet 130 and the second permanent magnet 230.

In Step S13, the second capsule robot 200 may be fixed with respect to the internal organ wall by protruding the second leg unit 240 to the internal organ wall in a state of being connected to the first capsule robot 100. In this state, the first capsule robot 100 and the second capsule robot 200 are fixed while pushing the internal organ wall by protruding the leg units. After that, the first capsule robot 100 inserts the protruded first leg unit 140 into the first housing 110. Accordingly, the first capsule robot and the second capsule robot are fixed by means of the second leg unit 240 of the second capsule robot.

In Step S14, the first capsule robot 100 moves forwards by a predetermined length by moving the first shaft 120 out of the first capsule robot 100. In another embodiment, the second capsule robot 200 may move the first capsule robot 100 forwards by a predetermined length as the second capsule robot 200 moves the second shaft 220 out of the second capsule robot 200 along with the above movement of the first shaft 120.

After that, in Step S15, the first capsule robot 100 is fixed with respect to the internal organ wall at the location moved by a predetermined length by protruding the inserted first leg unit 140 to the internal organ wall. In addition, the second capsule robot 200 inserts the second leg unit 240 into the second housing 210.

In Step S16, the second capsule robot 200 whose second leg unit 240 is inserted into the second housing 210 moves to the first capsule robot 100 which has moved forwards. In order to move the second capsule robot 200 toward the first capsule robot 100, the second capsule robot 200 may move toward the first capsule robot by a predetermined length by moving the second shaft 220 into the second capsule robot 200. In another embodiment, the first capsule robot 100 may pulls the second capsule robot by moving the first shaft 120 into the first capsule robot 100. In another embodiment, the second capsule robot may move toward the first capsule robot by simultaneously moving the first shaft 120 and the second shaft 220 in the same direction.

As described above, the second capsule robot 200 approaches the first capsule robot 100 and is connected thereto through the process of Steps S11-S16. In addition, in a state where the second capsule robot is fixed, the first capsule robot may advance, and in a state where the first capsule robot is fixed, the second capsule robot may advance, which makes forward movement.

Hereinafter, a mechanism of moving two connected capsule robots rearwards (namely, moving toward the second capsule robot) in a similar principle will be described.

First, as in Step S11 of FIG. 2, the second capsule robot 200 approaches the first capsule robot 100 and is connected thereto by means of the first and second permanent magnets 130, 230. After that, the second capsule robot 200 is fixed with respect to the internal organ wall by protruding the second leg unit 240 to the internal organ wall in a state of being connected to the first capsule robot. At this time, the first capsule robot 100 release the contact with the internal organ wall by inserting the protruded first leg unit into the first housing, moves toward the second capsule robot 200 by a predetermined length by moving the first shaft 120 into the first capsule robot 100, moves toward the second capsule robot 200 by a predetermined length moving the second shaft 220 into the second capsule robot 200 in a similar way, and then is fixed with respect to the internal organ wall at the location moved by a predetermined length by protruding the inserted first leg unit 140 to the internal organ wall.

After that, the second capsule robot 200 moves by a predetermined length in a direction opposite to the first capsule robot 100 by inserting the protruded second leg unit 240 into the second housing 210 and moving the second shaft 220 out of the second capsule robot 200, moving by a predetermined length in a direction opposite to the first capsule robot 100 by moving the first shaft 120 out of the first capsule robot 100 in a similar way, and then is fixed with respect to the internal organ wall at the location moved by a predetermined length by protruding the inserted second leg unit to the internal organ wall.

The first capsule robot 100 and the second capsule robot 200 connected by the above mechanism may freely move bi-directionally in the internal organ. This uniting and moving of the capsule robots may be regarded as being similar to movement of inchworm.

Here, the control units 160, 260 may control a moving speed of the connected capsule robots by adjusting a length of the shafts protruding out of the capsule robots, a protruding speed, and a protruding or inserting speed of the leg units.

[Separating and Discharging of Capsule Robots]

Figure 3:
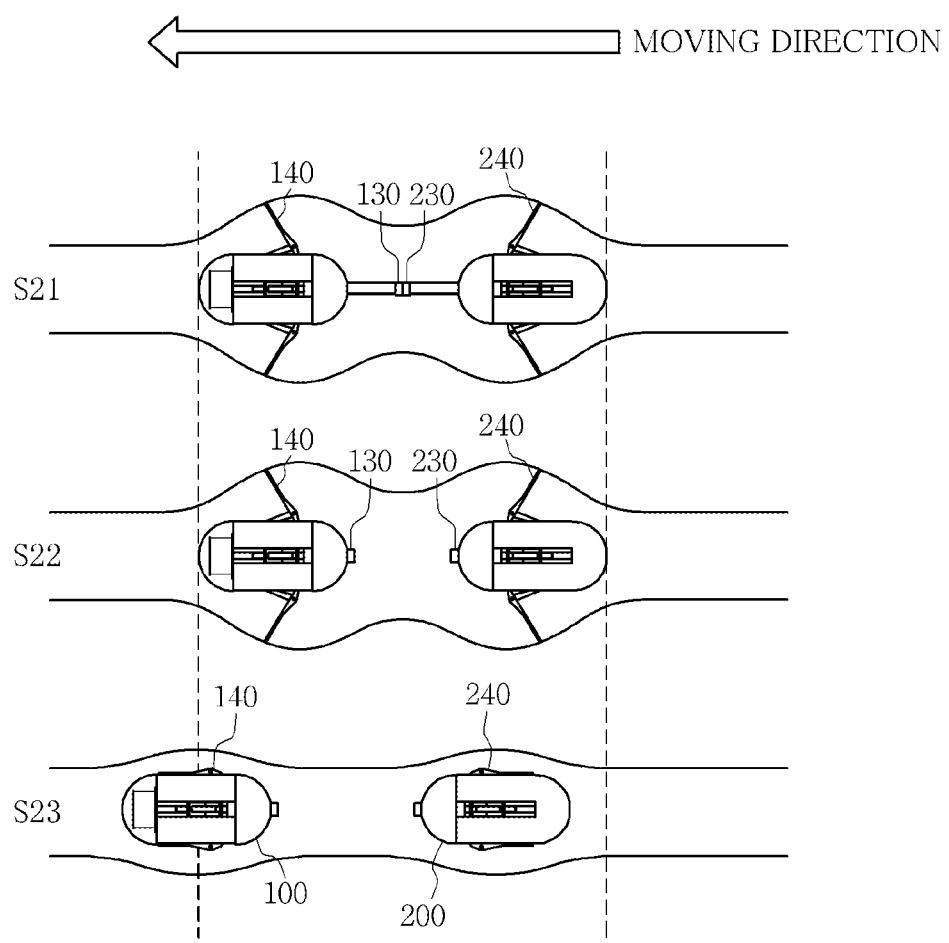
FIG. 3 is a diagram for illustrating a capsule robot separating mechanism of a motion control system for a capsule robot in a body according to an embodiment of the present disclosure.

FIG. 3 is a diagram for illustrating a capsule robot separating mechanism of a motion control system for a capsule robot in a body according to an embodiment of the present disclosure.

In Step S21, the first capsule robot 110 fixed to the internal organ wall by using the protruded first leg unit 140 and the second capsule robot 200 fixed to the internal organ wall by using the protruded second leg unit 240 are connected to face the shafts.

In Step S22, in a state of Step S21, the first capsule robot 100 moves the first shaft 120 into the first capsule robot 100. Similarly, the second capsule robot 200 moves the second shaft 220 into the second capsule robot 200. As a result, the first capsule robot 100 and the second capsule robot 200 are separated. In detail, two capsule robots connected to each other by an attractive force between the first permanent magnet 130 and the second permanent magnet 230 are separated from each other as the first and second shafts are mechanically pulled in opposite directions.

In Step S23, the first capsule robot 100 and the second capsule robot 200 separated from each other are also separated from the internal organ wall by inserting their leg units into the housings, respectively.

In detail, the first capsule robot 100 inserts the first leg unit 140 into the first housing 110 or the second capsule robot 200 inserts the second leg unit 240 into the second housing 210, thereby separating the first capsule robot or the second capsule robot from the internal organ wall. In other words, any one or both of two capsule robots may be separated from the internal organ wall. The capsule robot separated as above may be artificially removed at the anus or another body part of a patient.

[Case of Including an External Control Device]

In another embodiment, the first capsule robot 100 may further include a first camera 180. Similarly, the second capsule robot 200 may also further include a second camera 280. The first or second camera may be disposed at a side opposite to the extension hole, without being limited thereto. The first camera 180 and the second camera 280 may have a light emitting module to photograph a target in the dark inside of a body. The cameras 180, 280 may transmit the photographed image to the control units 160, 260.

Figure 4:
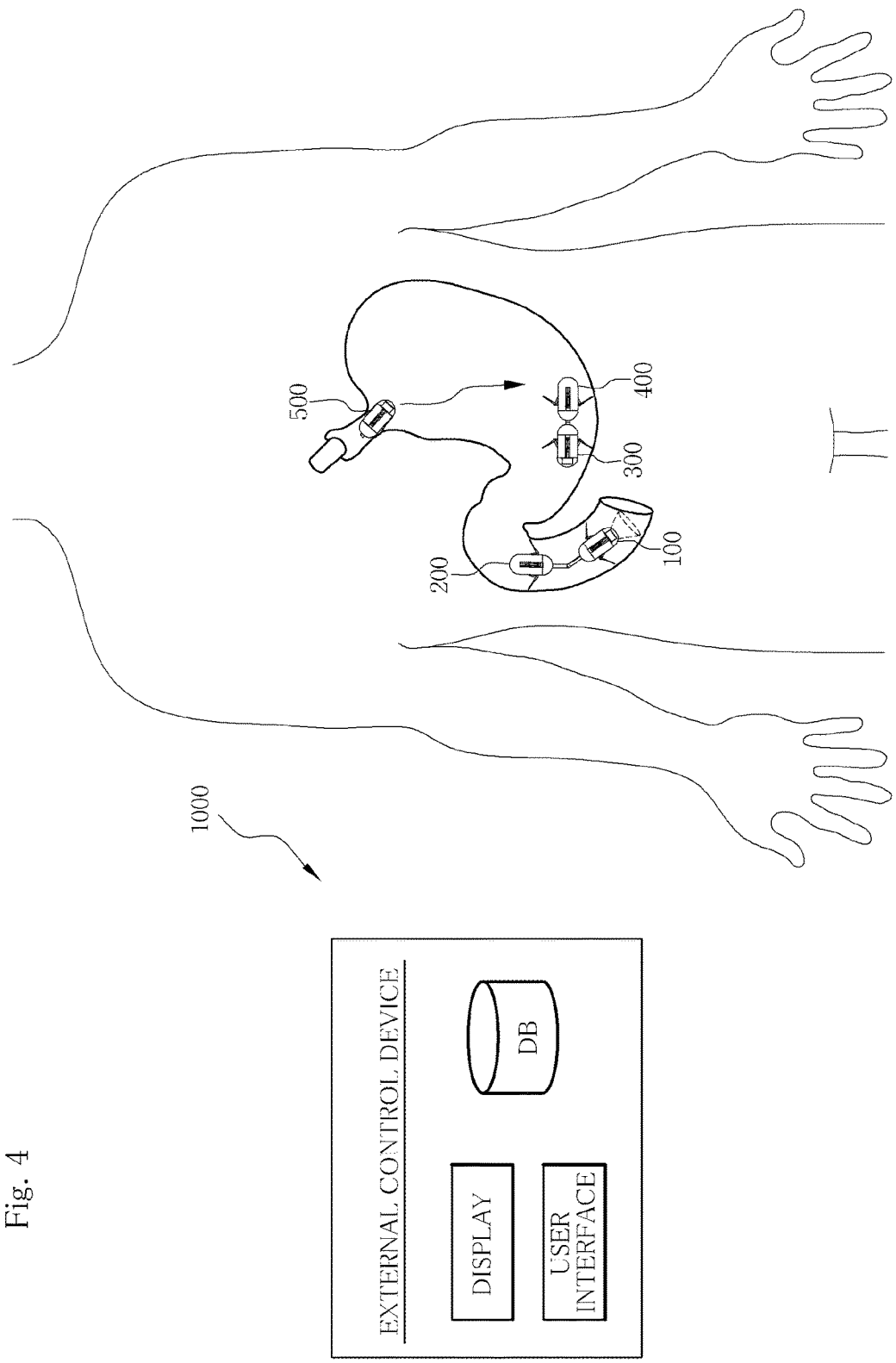
FIG. 4 is a diagram for illustrating an overall configuration of a motion control system 1000 for a capsule robot in a body according to another embodiment of the present disclosure.

FIG. 4 is a diagram for illustrating an overall configuration of a motion control system 1000 for a capsule robot in a body according to another embodiment of the present disclosure. The motion control system 1000 for a capsule robot in a body further includes an external control device provided out of a body, and the external control device may transmit an operation command or power to the first control unit 160 and the second control unit 260. In addition, the external control device may receive data from the capsule robots. The first control unit and the second control unit may control the first capsule robot and the second capsule robot according to the operation command, respectively. In another embodiment, the first capsule robot and the second capsule robot may operate by means of the operation command transmitted from the external control device.

In another embodiment, the external control device may include any display device, a database (DB) and a user interface.

In this embodiment, the first communication module 150 and/or the second communication module 250 may transmit image data respectively obtained at the first camera and/or the second camera to the external control device, and the display device of the external control device may display the transmitted image data. In addition, the database may store the image data.

The display device may be any display using LCD, LED, OLED, PDP, AMOLED or the like. The display device may display the image data, transmitted from a capsule robot, in real time.

In addition, the user interface gives a base for input in order to control operations of a capsule robot in a body and may include any software or input device (for example, a keyboard, a mouse, a touch screen, a robot master device).

Therefore, a user may directly control operations of the capsule robot in a body (for example, moving or photographing in the internal organ) by means of the external control device, and display and store data transmitted from the capsule robot. In addition, as shown in FIG. 4, a plurality of capsule robot pairs may be put into a body of a patient.

[Uniting of Three or More Capsule Robots]

In another embodiment, three or more capsule robots may be interconnected and move in a mechanism similar to the above. In still another embodiment, the second capsule robot 200 may further have a fourth extension hole formed in a side opposite to the second extension hole 221. Referring to FIG. 1, the fourth extension hole may be formed in a side where the camera 280 is present.

The second capsule robot may further include a fourth shaft which is movable bi-directionally along the fourth extension hole, and a fourth permanent magnet may be provided at an outer end of the fourth shaft. In other words, the second capsule robot includes two shafts so that two capsule robots may be connected at the front and rear of the second capsule robot.

In another embodiment, a third capsule robot may be further included. The structure and operation of the third capsule robot are similar to those of the second capsule robot illustrated in FIG. 2. In other words, the third capsule robot may include a third housing configuring an appearance, a third shaft configured to be movable bi-directionally along a third extension hole formed in one surface of the third housing, the third shaft having a third permanent magnet at an outer end thereof, a third leg unit configured to protrude outwards from the third housing and be inserted again into the third housing, and a third control unit for controlling operations of the third shaft and the third leg unit. The third capsule robot is connected to the second capsule robot as the fourth permanent magnet and the third permanent magnet comes into contact with each other by an attractive force.

If three capsule robots are connected as described above, the robot may have two joints. In this case, the connected capsule robots may have a greater length in comparison to two connected capsule robot, which may be utilized for a suitable usage. Here, the first capsule robot and the third capsule robot may include cameras.

While the exemplary embodiments have been shown and described, it will be understood by those skilled in the art that various changes in form and details may be made thereto without departing from the spirit and scope of the present disclosure as defined by the appended claims. In addition, many modifications can be made to adapt a particular situation or material to the teachings of the present disclosure without departing from the essential scope thereof. Therefore, it is intended that the present disclosure not be limited to the particular exemplary embodiments disclosed as the best mode contemplated for carrying out the present disclosure, but that the present disclosure will include all embodiments falling within the scope of the appended claims.

What is claimed is:

1. A motion control apparatus, comprising:
a first capsule robot comprising a first housing, a first shaft bi-directionally movable along a first extension hole formed in a surface of the first housing, wherein the first shaft comprises a first permanent magnet at an outer end of the first shaft, a first leg unit configured to protrude outwards from the first housing and insertable into the first housing, and a first control unit configured to control operations of the first shaft and the first leg unit; and
a second capsule robot comprising a second housing, a second shaft bi-directionally movable along a second extension hole formed in a surface of the second housing, wherein the second shaft comprises a second permanent magnet at an outer end of the second shaft, a second leg unit configured to protrude outwards from the second housing and insertable into the second housing, and a second control unit configured to control operations of the second shaft and the second leg unit,
wherein the first capsule robot is configured to be fixed at a first location on an internal organ wall by protruding the first leg unit to the internal organ wall, and
wherein the second capsule robot is configured to be connected to the first capsule robot as the first permanent magnet comes into contact with the second permanent magnet by an attractive force.

2. The motion control apparatus of claim 1,
wherein the first shaft further comprises a hinge enabling the first permanent magnet to rotate.

3. The motion control apparatus of claim 1,
wherein an outer end of the first leg unit and an outer end of the second leg unit are made of soft plastic or rubber.

4. The motion control apparatus of claim 1,
wherein the second capsule robot is configured to be fixed with respect to the internal organ wall by protruding the second leg unit to the internal organ wall while being connected to the first capsule robot,
wherein the first and second capsule robots are configured to move the first capsule robot by a distance from the first location to a second location by
the first capsule robot inserting the protruded first leg unit into the first housing and moving the first shaft out of the first capsule robot, and
the second capsule robot moving the second shaft out of the second capsule robot, and
wherein the first capsule robot is configured to be fixed at the second location by protruding the inserted first leg unit to the internal organ wall.

5. The motion control apparatus of claim 4,
wherein the second capsule robot is configured to move toward the first capsule robot by the distance by inserting the protruding second leg unit into the second housing and moving the second shaft into the second capsule robot.

6. The motion control apparatus of claim 4,
wherein the second capsule robot is configured to insert the protruded second leg unit into the second housing, and
wherein the first capsule robot is configured to move the second capsule robot toward the first capsule robot by the distance by moving the first shaft into the first capsule robot.

7. The motion control apparatus of claim 4,
wherein the first capsule robot is configured to move the first shaft into the first capsule robot, and wherein the second capsule robot is configured to move the second shaft into the second capsule robot so that the first capsule robot and the second capsule robot are separated from each other.

8. The motion control apparatus of claim 7,
wherein the first capsule robot is configured to insert the first leg unit into the first housing to separate from the internal organ wall, or the second capsule robot is configured to insert the second leg unit into the second housing to separate from the internal organ wall.

9. The motion control system apparatus of claim 1,
wherein the second capsule robot is configured to be fixed to the internal organ wall by protruding the second leg unit to the internal organ wall while being connected to the first capsule robot,
wherein the first and second capsule robots are configured to move the first capsule robot toward the second capsule robot by a distance from the first location to a second location by
the first capsule robot inserting the protruded first leg unit into the first housing and moving the first shaft into the first capsule robot, and
the second capsule robot moving the second shaft into the second capsule robot, and
wherein the first capsule robot is configured to be fixed with respect to the internal organ wall at the second location by protruding the inserted first leg unit to internal organ wall.

10. The motion control apparatus of claim 9,
wherein the first and second capsule robots are configured to move the second capsule robot by the distance in a direction opposite to the first capsule robot to a third location by
the second capsule first robot inserting the protruded second leg unit into the second housing and moving the second shaft out of the second capsule robot, and
the first capsule robot moving the first shaft out of the first capsule robot, and
wherein the second capsule robot is configured to be fixed with respect to the internal organ wall at the third location by protruding the inserted second leg unit to the internal organ wall.

11. The motion control apparatus of claim 1,
wherein the first capsule robot further comprises a first camera at a first surface, and the second capsule robot further comprises a second camera at a second surface.

12. The motion control apparatus of claim 11,
wherein the first capsule robot further comprises a first communication module and the second capsule robot further comprises a second communication module,
wherein the motion control system further comprises an external control device located outside of the internal organ wall,
wherein the first communication module or the second communication module is configured to transmit image data, obtained from the first camera or the second camera, to the external control device, and
wherein the external control device comprises a display device configured to display the transmitted data and a database configured to store the transmitted data.

13. The motion control apparatus of claim 1,
wherein the first capsule robot comprises a first communication module and the second capsule robot further comprises a second communication module,
wherein the motion control system further comprises an external control device located outside of the internal organ wall, wherein the external control device is configured to transmit an operation command or power to the first control unit and the second control unit, and wherein the first control unit and the second control unit are configured to control the first capsule robot and the second capsule robot, respectively, according to the operation command.

14. The motion control system for a module type capsule robot in a body according to claim 1, wherein the second capsule robot further includes:

a fourth extension hole formed at a side opposite to the second extension hole; and a fourth shaft configured to be movable bi-directionally along the fourth extension hole, wherein the fourth shaft includes a fourth permanent magnet at an outer end, wherein the motion control system further comprises a third capsule robot, which includes a third housing configuring an appearance, a third shaft configured to be movable directionally along a third extension hole formed at one surface of the third housing, wherein the third shaft included a third permanent magnet at an outer end, a third leg unit configured to protrude outwards from the third housing and be insertable into the third housing, a third communication module configured to transmit or receive a signal to/from another party, and a third control unit configured to control operations of third shaft, the third leg unit and the third communication module, and wherein the third capsule robot is configured to be connected to the second capsule robot as the fourth permanent magnet comes into contact with the third permanent magnet by an attractive force.

* * * * *